(12) United States Patent
Martin

(10) Patent No.: US 6,350,931 B1
(45) Date of Patent: Feb. 26, 2002

(54) TAMPON ASSEMBLY WITH DETACHABLE CLEANSING TOWELETTE PACKET

(76) Inventor: Doris E. Martin, 1914 Quayle Valley East, Missouri City, TX (US) 77459

(*) Notice: Subject to any disclaimer, the term of this patent is extended or adjusted under 35 U.S.C. 154(b) by 0 days.

(21) Appl. No.: 09/693,526

(22) Filed: Oct. 20, 2000

(51) Int. Cl.[7] ........................... A61F 13/15; B65D 69/00
(52) U.S. Cl. ................. 604/358; 604/904; 604/385.18; 206/225
(58) Field of Search ............................ 604/904, 385.17, 604/385.18, 385.01, 11–18; 206/225, 438, 440

(56) References Cited

U.S. PATENT DOCUMENTS

| | | | |
|---|---|---|---|
| 4,702,378 A | 10/1987 | Finkel et al. | 206/581 |
| 4,790,840 A | 12/1988 | Cortina | 604/385.1 |
| 5,261,531 A | 11/1993 | Nieves | 206/205 |
| 5,304,158 A | 4/1994 | Webb | 604/385.1 |
| 5,443,161 A | 8/1995 | Jonese | 206/581 |
| 5,569,230 A | 10/1996 | Fisher et al. | 604/385.1 |
| 5,582,605 A | 12/1996 | Lepie | 604/385.1 |
| 5,702,379 A | 12/1997 | Preiss | 604/385.1 |
| 5,986,165 A | 11/1999 | Moder et al. | 604/358 |
| 5,988,386 A | 11/1999 | Morrow | 206/581 |
| 6,004,307 A | 12/1999 | Colon et al. | 604/385.1 |

*Primary Examiner*—Dennis Ruhl

(57) ABSTRACT

A tampon assembly that includes a moistened, anti-bacterial towelette attached thereto that was removable by the user and also ensured the user had a cleansing wipe for freshening up as desired. The towelette is enclosed in a sealed packet that is adhesively held to a tubular portion of the tampon insertion device with a releasable, non-residue leaving adhesive in a manner to provide a slim line shape easily carried and includes a grasping tab to ensure easy removal of the sealed packet when needed.

1 Claim, 2 Drawing Sheets

# TAMPON ASSEMBLY WITH DETACHABLE CLEANSING TOWELETTE PACKET

TECHNICAL FIELD

The present invention relates to feminine hygiene products and more particularly to a tampon assembly with a detachable cleansing towelette packet that includes a tampon assembly including a tampon enclosed within a tampon insertion device having a tubular portion and a detachable cleaning towelette packet having a moistened, anti-bacterial towelette contained within a sealed, moisture tight package having one side surface thereof covered with a releasable, non-residue leaving adhesive and a grasping tab extending from one end thereof; the sealed, moisture tight package being wrapped at least once completely around the tubular portion of the tampon insertion device with the side surface thereof covered with the releasable, non-residue leaving adhesive positioned into adhesive connection with the exterior of the tubular portion of the tampon insertion device such that the grasping tab extends outward available for grasping by a user to unpeel the sealed, moisture tight package away from the tubular portion of the tampon insertion device so that the moistened, anti-bacterial towelette can be removed from the sealed, moisture tight package and used for personal cleansing and disinfecting prior to inserting the tampon with the tampon insertion device.

BACKGROUND ART

Many women desire to freshen up during the period between removing a tampon and inserting a new tampon. Although such freshening or cleansing is desirable, it is not always possible because there is no readily available cleansing device or facility. It would be desirable, therefore, to have a tampon assembly that included a moistened, anti-bacterial towelette attached thereto that was removable by the user and also ensured the user had a cleansing wipe for freshening up as desired.

GENERAL SUMMARY DISCUSSION OF INVENTION

It is thus an object of the invention to provide a tampon assembly with detachable cleansing towelette packet that includes a tampon assembly including a tampon enclosed within a tampon insertion device having a tubular portion and a detachable cleaning towelette packet having a moistened, anti-bacterial towelette contained within a sealed, moisture tight package having one side surface thereof covered with a releasable, non-residue leaving adhesive and a grasping tab extending from one end thereof; the sealed, moisture tight package being wrapped at least once completely around the tubular portion of the tampon insertion device with the side surface thereof covered with the releasable, non-residue leaving adhesive positioned into adhesive connection with the exterior of the tubular portion of the tampon insertion device such that the grasping tab extends outward available for grasping by a user to unpeel the sealed, moisture tight package away from the tubular portion of the tampon insertion device so that the moistened, anti-bacterial towelette can be removed from the sealed, moisture tight package and used for personal cleansing and disinfecting prior to inserting the tampon with the tampon insertion device.

Accordingly, a tampon assembly with detachable cleansing towelette packet is provided. The tampon assembly with detachable cleansing towelette packet includes a tampon assembly including a tampon enclosed within a tampon insertion device having a tubular portion and a detachable cleaning towelette packet having a moistened, anti-bacterial towelette contained within a sealed, moisture tight package having one side surface thereof covered with a releasable, non-residue leaving adhesive and a grasping tab extending from one end thereof; the sealed, moisture tight package being wrapped at least once completely around the tubular portion of the tampon insertion device with the side surface thereof covered with the releasable, non-residue leaving adhesive positioned into adhesive connection with the exterior of the tubular portion of the tampon insertion device such that the grasping tab extends outward available for grasping by a user to unpeel the sealed, moisture tight package away from the tubular portion of the tampon insertion device so that the moistened, anti-bacterial towelette can be removed from the sealed, moisture tight package and used for personal cleansing and disinfecting prior to inserting the tampon with the tampon insertion device.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein.

EXEMPLARY MODE FOR CARRYING OUT THE INVENTION

Figure 1:
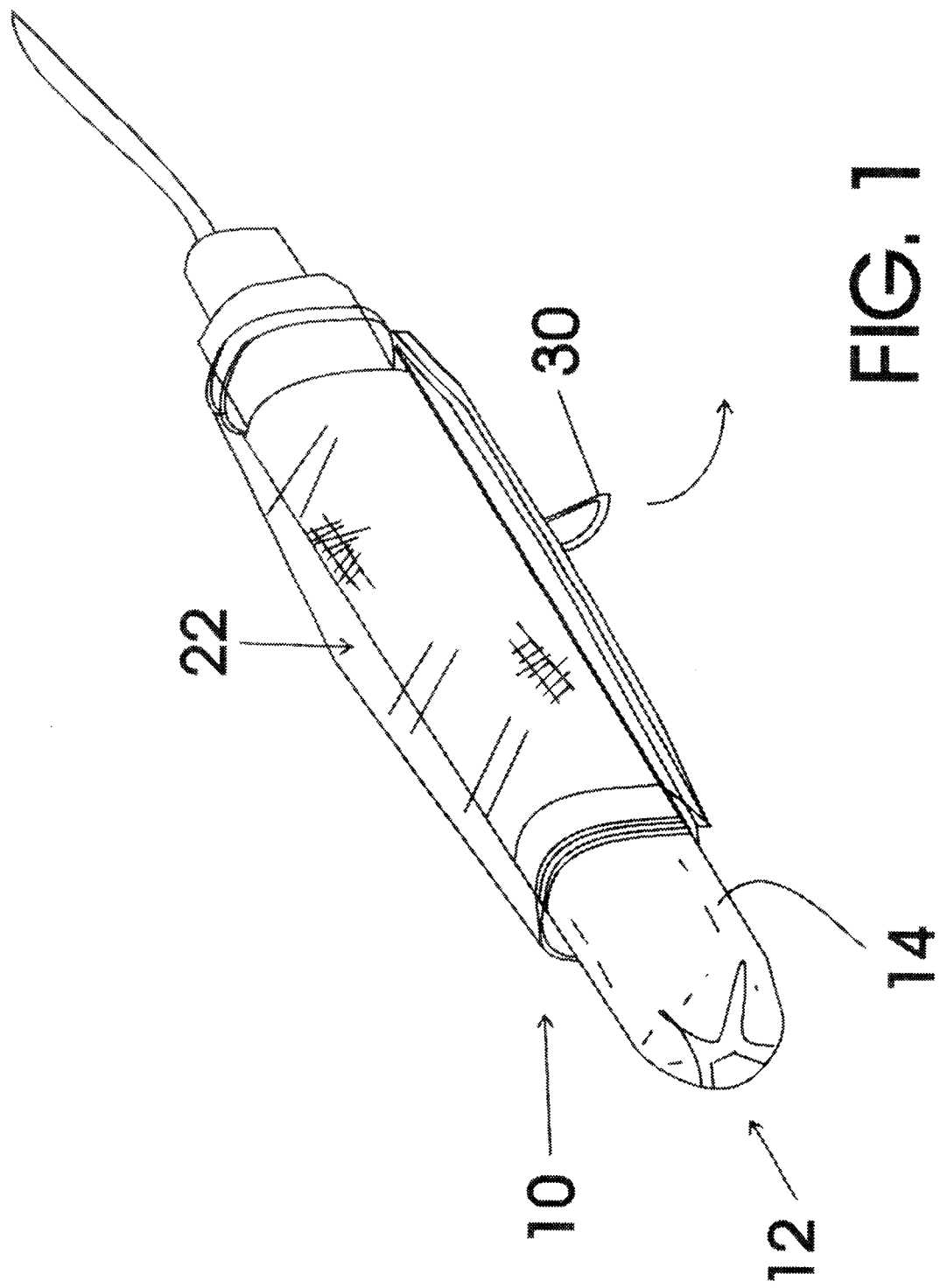
FIG. 1 is a perspective view of an exemplary embodiment of the a tampon assembly with detachable cleansing towelette packet with the sealed, moisture tight package containing the moistened, anti-bacterial towelette wrapped around the tubular portion of the tampon insertion device and adhesively attached thereto such that the grasping tab extends outward available for grasping by a user.
Figure 2:
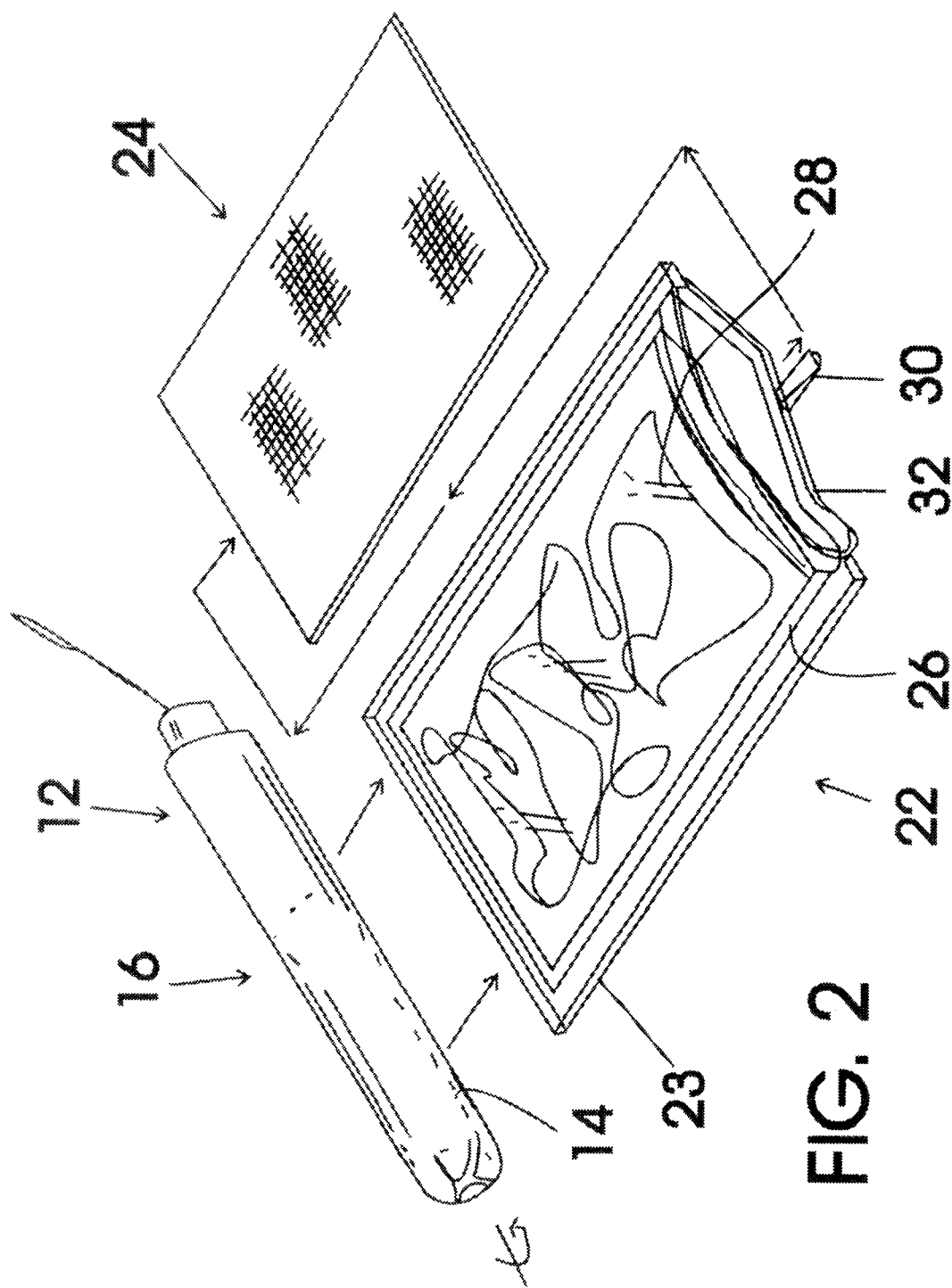
FIG. 2 is an exploded perspective view of the exemplary tampon assembly with detachable cleansing towelette packet of FIG. 1 with the sealed, moisture tight package detached from the tubular portion of the tampon insertion device and the moistened, anti-bacterial towelette removed from the sealed, moisture tight package by tearing open the edge of the package connected to the grasping tab.

FIGS. 1 and 2 show various aspects of an exemplary embodiment of the tampon assembly with detachable cleansing towelette packet of the present invention generally designated 10. Tampon assembly with detachable cleansing towelette packet 10 includes a tampon assembly, generally designated 12, including a tampon 14 (shown in dashed lines) enclosed within a tampon insertion device, generally designated 16, having a tubular portion 20; and a detachable cleaning towelette packet, generally designated 22.

Detachable cleaning towelette packet 22 includes a sealed moisture tight package 23 that sealably contains a moistened, anti-bacterial towelette, generally designated 24. Sealed, moisture tight package 23 is constructed from heat sealable plastic film and has one side surface 26 thereof covered with a releasable, non-residue leaving adhesive 28 and a grasping tab extending 30 from one end thereof 32. A releasable, non-residue leaving adhesive 28 is used to prevent adhesive residue form being inserted and left within the body during insertion of the tampon. End 32 of sealed, moisture tight package 23 is torn open by the user, (see FIG. 2), to remove moistened, anti-bacterial towelette 24 for use.

Sealed, moisture tight package 23 is wrapped at least once completely around tubular portion 16 of tampon insertion device 12 with the side surface 26 thereof covered with the releasable, non-residue leaving adhesive 28 positioned into adhesive connection with the exterior of the tubular portion 16 such that grasping tab 30 extends outward and is readily available for grasping by a user. This configuration provides a slim line package that allows the user to easily remove the detachable cleaning towelette packet 22.

In use, the user grasps grasping tab 30 and unpeels sealed, moisture tight package 23 away from tubular portion 16; tears open the end 32 of sealed moisture tight package 23, removes towelette 24 and then uses towelette 24 for person cleansing as desired.

It can be seen from the preceding description that a tampon assembly with detachable cleansing towelette packet has been provided.

It is noted that the embodiment of the tampon assembly with detachable cleansing towelette packet described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A tampon assembly with detachable cleansing towelette packet comprising:

a tampon assembly including a tampon enclosed within a tampon insertion device having a tubular portion; and a detachable cleaning towelette packet having a moistened, anti-bacterial towelette contained within a sealed, moisture tight package having one side surface thereof covered with a releasable, non-residue leaving adhesive and a grasping tab extending from one end thereof;

the sealed, moisture tight package being wrapped at least once completely around the tubular portion of the tampon insertion device with the side surface thereof covered with the releasable, non-residue leaving adhesive positioned into adhesive connection with the exterior of the tubular portion of the tampon insertion device such that the grasping tab extends outward available for grasping by a user to unpeel the sealed, moisture tight package away from the tubular portion of the tampon insertion device so that the moistened, anti-bacterial towelette can be removed from the sealed, moisture tight package and used for personal cleansing and disinfecting prior to inserting the tampon with the tampon insertion device.

* * * * *